United States Patent
Criel et al.

(10) Patent No.: US 9,841,412 B2
(45) Date of Patent: Dec. 12, 2017

(54) METHOD AND SYSTEM FOR DETERMINING THE VOLATILITY OF A FUEL

(71) Applicant: Plastic Omnium Advanced Innovation and Research, Brussels (BE)

(72) Inventors: Bjorn Criel, Sint-Martens-Lennik (BE); David Hill, Commerce Township, MI (US); Antoine Chaussinand, Brussels (BE)

(73) Assignee: Plastic Omnium Advanced Innovation and Research, Brussels (BE)

( * ) Notice: Subject to any disclaimer, the term of this patent is extended or adjusted under 35 U.S.C. 154(b) by 52 days.

(21) Appl. No.: 14/824,573

(22) Filed: Aug. 12, 2015

(65) Prior Publication Data
US 2016/0061802 A1    Mar. 3, 2016

Related U.S. Application Data

(60) Provisional application No. 62/045,389, filed on Sep. 3, 2014.

(30) Foreign Application Priority Data

Oct. 21, 2014 (EP) .................................... 14189730

(51) Int. Cl.
*G01N 33/22* (2006.01)
*G01L 7/00* (2006.01)
(Continued)

(52) U.S. Cl.
CPC ............. *G01N 33/22* (2013.01); *B60K 15/03* (2013.01); *F02D 41/0025* (2013.01);
(Continued)

(58) Field of Classification Search
CPC .... G01N 33/22; B60K 15/03; F02D 41/0025; F02M 37/0076; G01L 7/00; G01M 3/00
See application file for complete search history.

(56) References Cited

U.S. PATENT DOCUMENTS

| 5,878,727 A | 3/1999 | Huls |
| 2009/0114288 A1 | 5/2009 | Grant et al. |

(Continued)

FOREIGN PATENT DOCUMENTS

| EP | 1 801 394 A1 | 6/2007 |
| GB | 2 325 983 | 12/1998 |

OTHER PUBLICATIONS

European Search Report dated Apr. 20, 2015 in European Application 14189730.6, filed on Oct. 21, 2014.

*Primary Examiner* — Hezron E Williams
*Assistant Examiner* — David Z Huang
(74) *Attorney, Agent, or Firm* — Oblon, McClelland, Maier & Neustadt, L.L.P.

(57) ABSTRACT

A method for determining the volatility of fuel in a fuel storage system which entails: determining that a refueling event has occurred (210) and that the fuel storage system has subsequently been sealed (220); performing a first pressure measurement (230) at a first time after the determining; performing a second pressure measurement (240) at a second time, the second time occurring after the first time; determining a pressure evolution rate (250) from the first pressure measurement at the first time and the second pressure measurement at the second time; and deriving an estimation (260) of the volatility of the fuel from the pressure evolution rate.

18 Claims, 3 Drawing Sheets

(51) Int. Cl.
*G01M 3/00* (2006.01)
*F02M 37/00* (2006.01)
*F02D 41/00* (2006.01)
*B60K 15/03* (2006.01)

(52) U.S. Cl.
CPC ........... *F02M 37/0076* (2013.01); *G01L 7/00* (2013.01); *G01M 3/00* (2013.01); *B60K 2015/0321* (2013.01); *F02D 2200/0612* (2013.01)

(56) References Cited

U.S. PATENT DOCUMENTS

| | | | | |
|---|---|---|---|---|
| 2010/0332108 | A1* | 12/2010 | Kato | F02D 33/02 |
| | | | | 701/104 |
| 2013/0298872 | A1* | 11/2013 | Kojima | F02D 41/0025 |
| | | | | 123/446 |
| 2014/0297071 | A1* | 10/2014 | Dudar | F02D 41/22 |
| | | | | 701/22 |

* cited by examiner

METHOD AND SYSTEM FOR DETERMINING THE VOLATILITY OF A FUEL

FIELD OF THE INVENTION

The present invention pertains to the field of vehicular liquid storage systems, in particular fuel tank systems.

BACKGROUND

The volatility of fuel (e.g., the Reid Vapor Pressure (RVP)) is an essential parameter for the proper functioning of an internal combustion engine. In addition, it is important to know the value of this parameter to perform accurate leak detection.

International patent application publication no. WO2007071659, entitled "Method for the onboard determination of the volatility of a fuel", in the name of the present applicant, discloses a method for the onboard determination of the volatility of a fuel stored in a fuel tank, which is part of a fuel system controlled by a fuel system control unit (FSCU) and comprising pressure, temperature and fuel level sensors, according to which the FSCU uses the ideal gas law and measurements performed by the sensors in order to predict the distillation curve and/or the Driveability Index (DI) of the fuel. The method is used to adjust the amount of fuel to be injected in a mixing chamber of an internal combustion engine of a motor vehicle.

Another known device, disclosed in US 2010/0332108 A1, relies on a combination of pressure variation and temperature variation to produce an estimate of the Reid Vapor Pressure (RVP).

It is a disadvantage of the known methods and devices, that they require sufficiently different thermodynamic states of the system, in terms of temperature and pressure, to allow the calculation of the volatility of the fuel from the ideal gas law. As the temperature of the system evolves slowly, this implies that a relatively long time elapses before the determination of the volatility of the fuel can be completed.

SUMMARY OF THE INVENTION

It is an object of embodiments of the present invention to at least partially overcome the drawbacks of the prior art.

According to an aspect of the present invention, there is provided a method for determining the volatility of fuel in a fuel storage system, the method comprising: determining that a refueling event has occurred and that the fuel storage system has subsequently been sealed; performing a first pressure measurement at a first time after the determining; performing a second pressure measurement at a second time, the second time occurring after the first time; determining a pressure evolution rate from the first pressure measurement at the first time and the second pressure measurement at the second time; and deriving an estimation of the volatility of the fuel from the pressure evolution rate.

The fuel storage system is preferably a vehicular fuel system, such as the fuel system of a car or a truck with an internal combustion engine, comprising a fuel tank equipped with a filler pipe and one or more valves (e.g. a purge valve and a shut-off valve).

It is an advantage of the present invention that the determination of the volatility of the fuel is achieved by monitoring a return to partial pressure equilibrium (after perturbation of said equilibrium due to a refueling event), rather than a temperature evolution. The return to partial pressure equilibrium occurs at a relatively short time scale, such that the method according to the present invention yields a result much faster than the prior art method.

It is a further advantage of the present invention that the determination of the volatility of the fuel is linked to refueling events, which are the points in time at which the most significant discontinuities in volatility are to be expected. This is due to the fact that fuels originating from different suppliers have different compositions and therefore different physico-chemical properties. Between refueling events, the properties of the fuel stored in the fuel system evolve only very slowly, mainly due to ageing and evaporation of the most volatile components.

The present invention is based inter alia on the insight of the inventors that the stabilization of partial pressure ratio within the sealed tank leads to an observable evolution of the pressure in the tank. This pressure evolution can be measured by taking at least two pressure measurements with a short intervening time interval, and is indicative of the volatility of the fuel.

In an embodiment of the method according to the present invention, the first time is less than 1 minute after the determining, preferably less than 15 seconds after the determining.

It is an advantage of this embodiment that the estimation of the volatility is closely linked to the moment of refueling, which is the moment at which a change in volatility is most likely to occur, and which is the moment at which the perturbation of the system's equilibrium occurs. This embodiment is based on the insight of the inventors that it is not advantageous to perform the estimation of the volatility too long after refueling, because in time the system may have approached its new equilibrium so closely that pressure evolution rate can no longer be detected.

In an embodiment of the method according to the present invention, the deriving further takes into account one or more of an ambient temperature, a fuel temperature, a vapor dome temperature, a fuel level, a refueling rate, a canister load, an ambient pressure, fuel system design parameters, and an altitude of the fuel storage system.

It is an advantage of this embodiment that a more accurate estimate of the volatility can be obtained, by including additional parameters in the derivation. This embodiment is based on the insight of the inventors that each of the listed parameters physically influences the rate at which the pressure in the system evolves, and that the contribution of the volatility can be more accurately estimated by accounting for the contribution of one or more other relevant parameters.

In an embodiment of the method according to the present invention, the first pressure measurement and the second pressure measurement are carried out at a vapor dome inside the fuel tank.

This embodiment is particularly advantageous in existing fuel storage systems that are already equipped with a pressure sensor in the fuel tank.

In an embodiment of the method according to the present invention, the first pressure measurement and the second pressure measurement are carried out outside the fuel tank, in a cavity that is in fluid communication with a vapor dome inside the fuel tank. The pressure measurement can be either a relative pressure measurement or an absolute pressure measurement.

It is an advantage of this embodiment that the method can be applied with a pressure sensor positioned at any suitable place in the fuel storage system, without necessitating a redesign of the assembly of accessories that are arranged inside the fuel tank.

According to an aspect of the present invention, there is provided a computer program product comprising code means configured to cause a processor to carry out the method described above.

According to an aspect of the present invention, there is provided a fuel storage system comprising a fuel tank, means for detecting a refueling event of the fuel tank, means for detecting sealing of said fuel storage system, a pressure sensor, and a controller operatively connected to said means for detecting a refueling event, said means for detecting sealing of said fuel storage system, and said pressure sensor; wherein said controller is configured to carry out the method described above.

In an embodiment of the fuel storage system according to the present invention, the pressure sensor is arranged in a vapor dome inside the fuel tank.

In an embodiment of the fuel storage system according to the present invention, the pressure sensor is arranged in a cavity that is in fluid communication with a vapor dome inside the fuel tank.

According to an aspect of the present invention, there is provided a motor vehicle comprising the fuel storage system described above.

The technical effects and advantages of the computer program product, the fuel storage system, and the motor vehicle according to the present invention correspond, mutatis mutandis, to those of the corresponding embodiments of the method according to the present invention.

BRIEF DESCRIPTION OF THE FIGURES

These and other technical aspects and advantages of embodiments of the present invention will now be described in more detail with reference to the accompanying drawings, in which.

DESCRIPTION OF EMBODIMENTS

Figure 1:
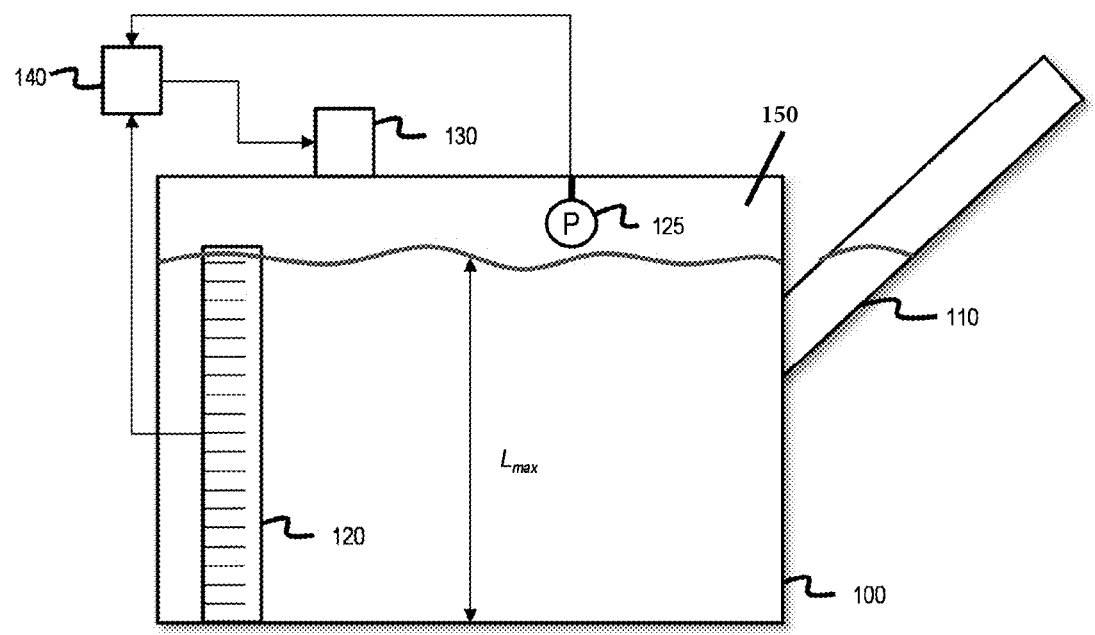
FIG. 1 presents a schematic overview of a vehicular liquid storage system in which the present invention can be used.

Throughout the present description, the term "shut-off valve" is used to designate a valve that can be opened or closed to control the maximum fill level that can be achieved in the tank. The shut-off valve may be of a kind that is biased open and mechanically closes when the liquid reaches a certain level (e.g. a float valve), or it may be an electronically controlled valve which can be opened or closed, as the case may be, by an electronic signal, with a view to allowing or stopping a refueling operation. Without loss of generality, the present description describes an embodiment of the invention in which the shut-off valve is an electronic valve.

It is well known from thermodynamics that any substance which is present in a closed system in liquid form and in gaseous form will be subject to constant transition of molecules between both phases. Eventually, the rate at which molecules from the gas phase condense into the liquid phase will equal the rate at which molecules from the liquid phase evaporate into the gas phase, such that an equilibrium is established. This equilibrium occurs at a certain partial pressure of the vapor in the gas phase, known as the vapor pressure of the liquid, the value of which is a characteristic of the liquid which depends only on the temperature of the system. Thus, the vapor pressure of a liquid is a measure of its volatility.

The present invention is based inter alia on the insight of the inventors that when a fuel storage system is opened in order to start a refueling operation, i.e. the cap is removed from the filler neck and a shut-off valve is opened, the overall pressure of the gaseous phase in the fuel tank will drop towards the atmospheric pressure, and, in particular, the partial pressure of the fuel vapor will drop below the vapor pressure for the given temperature, as vaporizing fuel escapes from the tank and fails to contribute to the establishment of a condensation-evaporation equilibrium.

The present invention is further based on the insight of the inventors that during refueling, a new amount of liquid fuel, with its own characteristic volatility, is added to the fuel system in conditions which prevent the formation of a pressure equilibrium (agitation of the liquid due to the addition of liquid fuel, evaporation through the open cap and shut-off valve). Only when the fuel storage system is sealed again, will the system be capable of reestablishing a liquid-gas equilibrium. The evolution of the system towards the new equilibrium will be observable as a gradual change in pressure.

The present invention is further based on the insight of the inventors that the rate at which the system pressure increases from a sub-equilibrium value towards its equilibrium, is characteristic of the volatility of the fuel. Thus, surprisingly, it is not necessary to wait until the equilibrium vapor pressure has been reached, to obtain an estimation of the volatility of the liquid. By using the pressure evolution rate, rather than the absolute vapor pressure, the volatility estimate can be obtained in a much shorter time.

Reid vapor pressure (RVP) is a common measure of the volatility of gasoline. It is defined as the absolute vapor pressure exerted by a liquid at 37.8° C., as determined by a standardized test method (ASTM-D-323). Throughout this application, the volatility of the fuel to be determined may be its RVP, any other vapor pressure characteristic, or any other suitable measure of the fuel's volatility.

The vehicular liquid storage system of the present invention is preferably a liquid fuel storage system for a vehicle having an internal combustion engine (liquid fuel types may include ethanol, gasoline, liquefied petrol gas, diesel oil, and the like). However, the invention may also be used in conjunction with other vehicular liquids, for which it may be useful to determine a volatility, for instance to allow for accurate leak detection.

FIG. 1 presents a schematic overview of a vehicular fuel storage system, in which the present invention can be used. The system comprises a tank 100, in which a level gauge 120 is arranged. Without loss of generality, a tank 100 of a very simple geometry is shown; in reality, the tank may comprise multiple compartments, as is the case for a so-called "saddle tank". In that case, several level gauges would be present for the respective compartments, and the method according to the invention could be applied mutatis mutandis on the basis of the level readings from the compartments with the highest fill level.

When, during a filling operation (i.e., when liquid is added to the tank via filler pipe 110), the liquid level reaches a predetermined level $L_{max}$, a controller 140, which receives the level signal from the level gauge 120, causes a shut-off valve 130 to close, which causes the filling operation to stop (The valve 130 is generally in fluid communication with the atmosphere via a venting line, optionally via a vapor absorbing canister (not shown).

The filling operation normally takes place with an open shut-off valve 130; in that situation, the inflow of liquid will decrease the available volume for the vapor-air mixture, which is being forced out through the valve 130.

If the shut-off valve 130 is opened and left open when a liquid column of a certain height is still present in the filler pipe, some of the vapor-air mixture will escape through the valve 130 towards the atmosphere (optionally, via the canister), until the pressure in the vapor dome has decreased to atmospheric pressure. Only when the system sealed, i.e. the shut-off valve 130 is closed and a cap is placed to close the filler pipe 110, a new pressure equilibrium will be formed, as the partial pressure of the fuel vapor in the gaseous phase will rise to the vapor pressure for the given temperature.

A pressure sensor 125, connected to the controller 140, is arranged to measure the pressure in the tank 100. In the illustrated example, the pressure sensor 125 is placed directly in the vapor dome 150 inside the tank. In other embodiments, it may be placed in any other convenient part of the fuel storage system
which is in fluid communication with the vapor dome.

The described system may be used to determine the vapor pressure of the stored liquid. In all internal combustion engines, it is necessary to measure fuel vapor pressure to control the fuel injection amount, the injection timing, the ignition timing, and others. It is also advantageous to know the fuel volatility in order to perform accurate leak detection.

Figure 2:
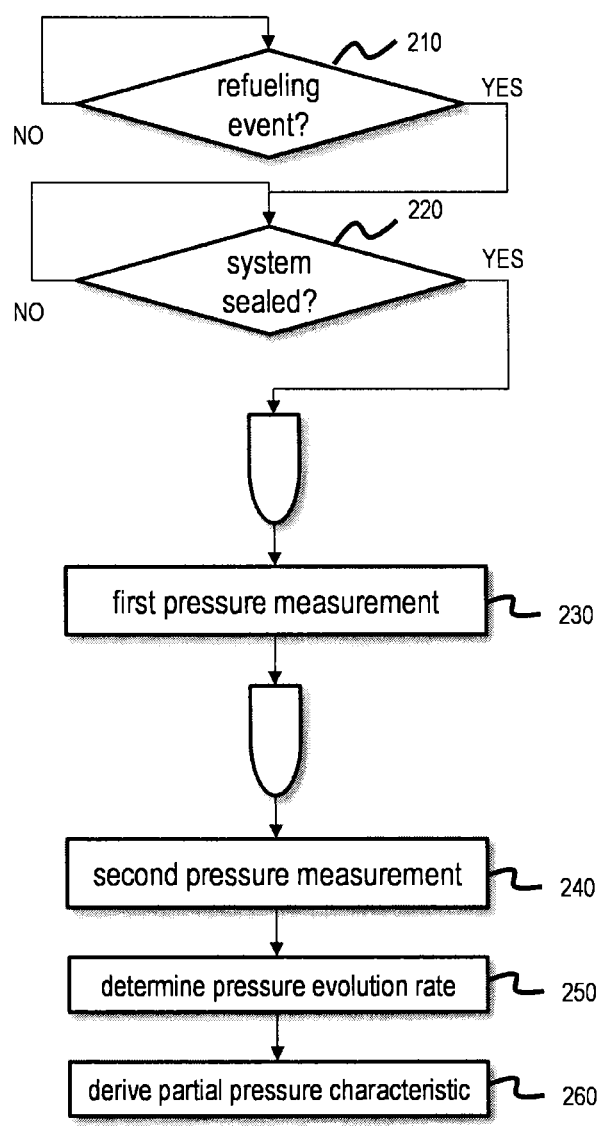
FIG. 2 provides a flow chart of an embodiment of the method according to the present invention.

FIG. 2 provides a flow chart of a method according to an embodiment of the present invention, for determining the volatility of fuel in a fuel storage system.

In a first step, the method comprises determining that a refueling event has occurred 210 and that the fuel storage system has subsequently been sealed 220.

The detection of the sealing may include a verification of the state of the shut-off valve and the actuation (if necessary) and verification of any other valves (not illustrated). In absence of detection verification, a timer could trigger to move to the next step.

Figure 3:
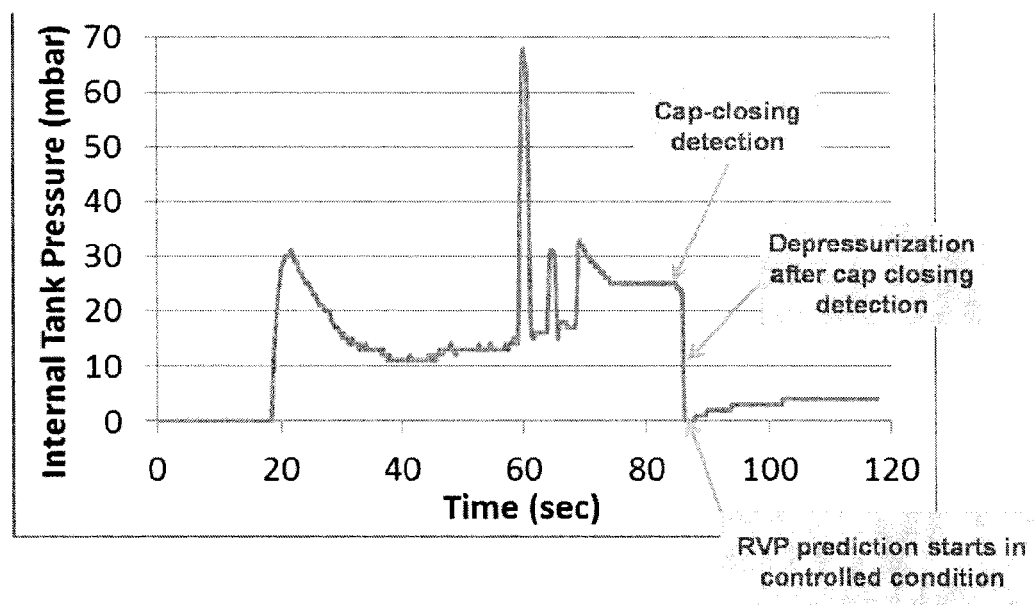
FIG. 3 is an exemplary pressure/time diagram representing a refueling operation.

The detection of the sealing also includes the detection of the closing of the cap of the filler pipe, which may for example be a built-in cap or a traditional screw-on or click-on cap. This detecting may happen in any known way, including by optical or electromechanical means. In a particularly advantageous embodiment, the detection of the closing of the cap is performed by monitoring the pressure inside the fuel tank. As the open filler pipe provides an escape path for evaporating fuel, the pressure of the unsealed system will tend to evolve towards atmospheric pressure. If the cap has been closed, the pressure in the tank will stabilize and eventually rise towards an equilibrium as described above. This effect is illustrated in the pressure/time diagram of FIG. 3, where the cap is closed at 75 s, causing the pressure drop which had started at the end of the refueling operation to stop. When this stabilization of the pressure is detected for approximately 10 s (exemplary value), it is interpreted as the closing of the cap. The monitoring with a view to detecting the presence of the cap may occur in a manner analogous to what will be described in connection with steps 230-250.

In a next step, a first pressure measurement is performed 230 at a first time after determining that the system has been sealed. This first time is preferably less than 1 minute after this determination, and more preferably less than 15 seconds after this determination. In this manner, the estimation of the volatility remains temporally closely linked to the most recent refueling operation and before the car has moved from the refueling station. Once fuel movement is generated inside the tank by the car's movement, the noise on the pressure measurement will be increased and the rate of vapor evaporation may change due to the increased surface area of the liquid to gas interface.

In the time between the detection of the sealing of the system 220 and the first pressure measurement 230, an additional pressure release may optionally be performed, to ensure that the pressure build-up will start from within fixed internal tank pressure boundaries. This optional pressure release is illustrated in the pressure/time diagram of FIG. 3, at approximately 85 s. The pressure build-up as the system evolves towards equilibrium is illustrated in the pressure/time diagram of FIG. 3 in the range between 85 s and 120 s.

A second pressure measurement is performed 240 at a second time, after the first time. The interval between the first time and the second time should be chosen sufficiently long to see a significant rise in pressure. Exemplary values of the interval are 5, 10, 20, and 30 seconds. The skilled person will be able to determine other suitable intervals by means of routine experiments.

The pressure measurements 230, 240 may be carried out at a vapor dome inside the fuel tank, or in any cavity that is in fluid communication with the vapor dome.

A pressure evolution rate is determined 250 from the first pressure measurement at the first time and the second pressure measurement at the second time. This determination may simply consist of calculating the slope Δp/Δt of the pressure (time) line connecting the two measurement points, where Δp is the pressure difference between the two measurement points, and Δt is the time interval between the two measurement points. While the measurement procedure has been described as consisting of two discrete measurements, the skilled person will appreciate that it is also possible to perform additional measurements or continuous pressure monitoring, to obtain a more accurate measure of the pressure evolution rate.

Finally, an estimation of the volatility of the fuel is derived 260 from the pressure evolution rate. The estimation may be carried out by using a formula of the following form:

$$RVP = a \times \frac{\Delta p}{\Delta t} + b \times T + c \times \frac{\Delta p}{\Delta t} \times T$$

where RVP represents the volatility of the fuel in terms of its Reid Vapor Pressure, T is the system temperature, and a, b, and c are coefficients which may be obtained by calibration.

The derivation of the volatility of the fuel may further take into account one or more of an ambient temperature, a temperature fuel temperature, a fuel level, a refueling rate, a canister load, an ambient pressure, and an altitude of the fuel storage system. In order to reduce calibration time the formula may also include fuel system design parameters, so the formula would be generic for different fuel systems, which would considerably reduce the calibration time and associated costs.

The present invention also pertains to a vehicular liquid storage system (see also FIG. 1) comprising a controller 130 configured to carry out the methods described above. The controller 130 may be implemented in dedicated hardware (e.g., ASIC), configurable hardware (e.g., FPGA), programmable components (e.g., a DSP or general purpose processor with appropriate software), or any combination thereof. The same component(s) may also include other functions.

While the invention has been described hereinabove with reference to specific embodiments, this was done to clarify and not to limit the invention. The skilled person will appreciate that various modifications and different combinations of disclosed features are possible without departing from the scope of the invention.

The invention claimed is:

1. A method for determining the volatility of fuel in a fuel storage system, the method comprising:
    determining that a refueling event has occurred and that the fuel storage system has subsequently been sealed;
    performing, by means of a pressure sensor in the fuel storage system, a first pressure measurement in the fuel storage system at a first time after the determining;
    performing, by means of the pressure sensor, a second pressure measurement in the fuel storage system at a second time, the second time occurring after the first time;
    determining, by means of a controller, a pressure evolution rate from the first pressure measurement at the first time and the second pressure measurement at the second time; and
    deriving an estimation of the volatility of the fuel from said pressure evolution rate.

2. The method according to claim 1, wherein said first time is less than 1 minute after said determining that a refueling event has occurred.

3. The method according to claim 1, wherein said deriving further takes into account one or more of an ambient temperature, a fuel temperature, a vapor dome temperature, a fuel level, a refueling rate, a canister load, fuel system design parameters, an ambient pressure, and an altitude of the fuel storage system.

4. The method according to claim 1, wherein said first pressure measurement and said second pressure measurement are carried out at a vapor dome inside a fuel tank comprised in said fuel storage system.

5. The method according to claim 1, wherein said first pressure measurement and said second pressure measurement are carried out outside a fuel tank comprised in said fuel storage system, in a cavity located outside the fuel tank and that is in fluid communication with a vapor dome inside said fuel tank.

6. A fuel storage system comprising:
    a fuel tank;
    means for detecting a refueling event of said fuel tank;
    means for detecting sealing of said fuel storage system;
    a pressure sensor; and
    a controller operatively connected to said means for detecting a refueling event, said means for detecting sealing of said fuel storage system, and said pressure sensor; wherein said controller is configured to carry out the method according to claim 1.

7. The fuel storage system according to claim 6, wherein said pressure sensor is arranged in a vapor dome inside said fuel tank.

8. The fuel storage system according to claim 6, wherein said pressure sensor is arranged in a cavity that is in fluid communication with a vapor dome inside said fuel tank.

9. A motor vehicle comprising the fuel storage system according to claim 6.

10. A method for determining the volatility of fuel in a fuel storage system, the method comprising:
    determining, by means of a sensor of a level of fuel in the fuel storage system, that a refueling event has occurred and determining that the fuel storage system has subsequently been sealed;
    performing, by means of a pressure sensor in the fuel storage system, a first pressure measurement in the fuel storage system at a first time after the determining;
    performing, by means of the pressure sensor, a second pressure measurement in the fuel storage system at a second time, the second time occurring after the first time;
    determining, by means of a controller, a pressure evolution rate from the first pressure measurement at the first time and the second pressure measurement at the second time; and
    deriving a reid vapor pressure of the fuel from said pressure evolution rate.

11. The method according to claim 10, wherein said first time is less than 1 minute after said determining that a refueling event has occurred.

12. The method according to claim 10, wherein said deriving further takes into account one or more of an ambient temperature, a fuel temperature, a vapor dome temperature, a fuel level, a refueling rate, a canister load, fuel system design parameters, an ambient pressure, and an altitude of the fuel storage system.

13. The method according to claim 10, wherein said first pressure measurement and said second pressure measurement are carried out at a vapor dome inside a fuel tank comprised in said fuel storage system.

14. The method according to claim 10, wherein said first pressure measurement and said second pressure measurement are carried out outside a fuel tank comprised in said fuel storage system, in a cavity that is in fluid communication with a vapor dome inside said fuel tank.

15. A fuel storage system comprising:
    a fuel tank;
    means for detecting a refueling event of said fuel tank;
    means for detecting sealing of said fuel storage system;
    a pressure sensor; and
    a controller operatively connected to said means for detecting a refueling event, said means for detecting sealing of said fuel storage system, and said pressure sensor; wherein said controller is configured to carry out the method according to claim 10.

16. The fuel storage system according to claim 15, wherein said pressure sensor is arranged in a vapor dome inside said fuel tank.

17. The fuel storage system according to claim 15, wherein said pressure sensor is arranged in a cavity that is in fluid communication with a vapor dome inside said fuel tank.

18. A motor vehicle comprising the fuel storage system according to claim 15.

* * * * *